United States Patent [19]

Weiss et al.

[11] Patent Number: 5,055,043
[45] Date of Patent: Oct. 8, 1991

[54] DENTAL FLUID CONTROL APPARATUS

[76] Inventors: Ervin Weiss, Lipsky 9, Tel Aviv; Zeev Ram, Yaacov 9, Rehovoth, both of Israel

[21] Appl. No.: 554,489

[22] Filed: Jul. 19, 1990

[51] Int. Cl.$^5$ .................. A61G 17/02; A61C 1/07; A61C 1/10; A61C 1/12
[52] U.S. Cl. .................. 433/86; 433/80; 433/82
[58] Field of Search .................. 433/80, 82, 84, 86, 433/88

[56] References Cited

U.S. PATENT DOCUMENTS

| | | | |
|---|---|---|---|
| 4,021,921 | 5/1977 | Detaille | 433/80 |
| 4,302,185 | 11/1981 | Hall | 433/27 |
| 4,315,742 | 2/1982 | Nash et al. | 433/86 |
| 4,331,422 | 5/1982 | Heyman | 433/125 |
| 4,820,152 | 4/1989 | Warrin et al. | 433/86 |

FOREIGN PATENT DOCUMENTS

| | | | |
|---|---|---|---|
| 2829271 | 1/1980 | Fed. Rep. of Germany | 433/82 |
| 3523026 | 1/1987 | Fed. Rep. of Germany | 433/80 |

*Primary Examiner*—John J. Wilson
*Assistant Examiner*—Cindy Cherichetti
*Attorney, Agent, or Firm*—Benjamin J. Barish

[57] ABSTRACT

Dental apparatus includes a tank of compressed sterile oxygen, or another compressed gas such as nitrogen, a source of a pressurized treatment liquid, and valves for coupling the oxygen tank or treatment liquid to the water inlet of the dental unit enabling the dental unit to be used for a wide variety of dental treatments, particularly when using a triple syringe for rinsing the canals in root canal treatment, or when using an ultrasonic scaler for dislodging hard deposits and stain.

12 Claims, 1 Drawing Sheet

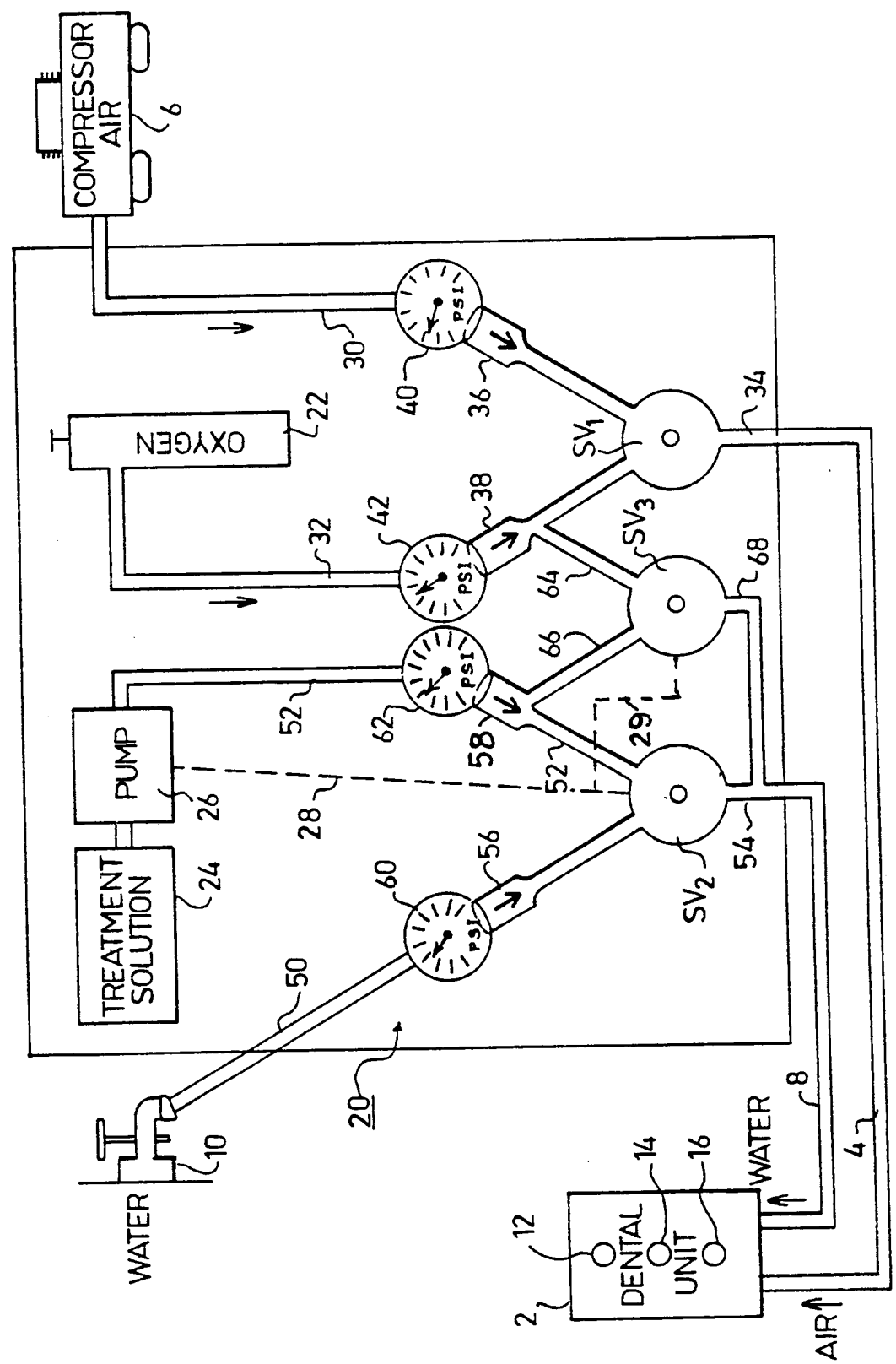

DENTAL FLUID CONTROL APPARATUS

FIELD AND BACKGROUND OF THE INVENTION

The present invention relates to dental apparatus, and particularly to apparatus for use with a dental unit of the conventional type for driving and/or cooling various dental appliances to be coupled to the dental unit. The invention also relates to a method for performing a dental or other medical operation on a person.

The conventional dental unit, as commonly found in dental offices, includes an air inlet to be coupled to a source of pressurized air, a water inlet to be coupled to a source of pressurized water usually the water tap, and outlet couplings for coupling various dental appliances to be used in treating the patient. The various dental appliances commonly used include high-speed turbine drills, slow-speed drills, triple syringes and ultrasonic scalers.

High-speed turbine drill is driven by compressed air at speeds as high as 400,000 rpm and is cooled by a spray of water and air. Such a drill is used for making incisions in hard tissue, such as teeth, while preparing a space where restoration is to be executed or while filing down a tooth for fitting a crown. High-speed turbine drills are also used for incisions of bone tissue in the jaw during surgical procedures such as extraction, periodontal surgery, and the like.

Slow-speed drills are driven by air or electricity at low speeds from 500 to 50,000 rpm. Such drills are used for cleaning teeth from decay processes (caries), for polishing teeth, and for performing implants of titanium screw and/or teeth in the jawbone.

Triple syringes are used for delivering water, compressed air, or both, through a nozzle to clean, rinse and dry various treated areas such as tooth tissue, root canal, gum tissue and bone tissue.

Ultrasonic scalers are instrument tips attached to a transducer through which high-frequency current causes vibrations of approximately 20,000–30,000 cps in conjunction with a stream of water to remove hard deposits (e.g., calculus) and stain, and to smooth the surface of the root of the tooth. Such instruments are also used in curettage procedures, i.e., for removing necrotic tissue lining the soft tissue wall of periodontal pockets.

The foregoing dental appliances are frequently applied to areas of an open wound. Since such appliances are driven and/or cooled by air or water (usually tap water) from the pressurized water source and by the air from the source of compressed air, there is a risk of contaminating the open wound with chemicals, bacteria, spores and/or viruses contained in the water and air. While various kinds of filters are commonly used, such filters are generally inefficient for removing all the above sources of contamination, and indeed in many cases the filter itself becomes a source of secondary infection by bacteria or other contaminating elements contained within it.

OBJECTS AND SUMMARY OF THE INVENTION

An object of the present invention is to provide dental apparatus particularly, but not exclusively, for use with a dental unit of the above type, which dental apparatus provides a number of advantages in the above respects as will be described more particularly below.

According to one aspect of the present invention, there is provided dental apparatus for use with a dental unit having a water inlet to be coupled to a source of pressurized water for driving and/or cooling dental appliances to be coupled to the dental unit, or for flushing the treatment site; the dental apparatus comprising: a tank of compressed oxygen; a source of a pressurized liquid; and valve means for coupling the tank of compressed oxygen and the source of pressurized liquid to the water inlet of the dental unit.

The dental unit also includes an air inlet connectible to a source of compressed air; and the valve means includes: means for selectively coupling the air inlet of the dental unit to the source of compressed air or to the tank of compressed oxygen; and means for selectively coupling the water inlet of the dental unit to the source of pressurized water, to the container for a treatment solution, or to both the container for a treatment solution and the tank of compressed oxygen.

According to another aspect of the present invention, there is provided dental apparatus for use with a dental unit having an air inlet to be coupled to a source of compressed air and a water inlet to be coupled to a source of pressurized water for driving and/or cooling dental appliances to be coupled to the dental unit; said dental apparatus comprising: a tank of compressed oxygen; a first selector valve for selectively coupling said air inlet of the dental unit either to said source of compressed air or to said tank of compressed gas; a container for a treatment solution; and a second selector valve for selectively coupling said water inlet of the dental unit either to said source of pressurized water or to said container of treatment solution.

According to a further feature in the described preferred embodiment, the dental apparatus further includes a third selector valve permitting the water inlet of the dental unit also to be connected to both the tank of compressed gas and container for a pressurized treatment solution so as to apply a mixture of the treatment solution and pressurized gas via the water inlet to the dental appliance coupled thereto.

It will thus be seen that dental apparatus enables the dentist to utilize the compressed oxygen in the tank instead of the conventional compressed air, and the treatment solution instead of water, for driving and/or cooling the dental appliance coupled to the conventional dental unit, or for rinsing the site of the dental treatment. An oxygen tank is usually present in a dental office for general anesthesia and/or for emergencies. Both the compressed oxygen, and the treatment solution are preferably sterile to thereby reduce the risk of infection.

The treatment solution may not only be sterile, but may also be or include various reagents. For example, it may be a physiologic-saline concentration solution, or a hypotonic or hypertonic solution. It may also include a germicide, antibiotic, antiseptic, antiviral, antifungal, analgesic, anti-inflammatory, vasoconstrictor flouride or another agent.

When a triple syringe is coupled to the dental unit, the treatment solution and/or sterile gas (e.g., oxygen) can be used especially for rinsing the canals in root canal treatment and the areas which are undergoing surgery. The electrical heater included in the conventional dental unit may also be used for heating the treatment solution or gas in the tank to body temperature so as to minimize discomfort and possible tissue damage.

The invention is particularly advantageous when using an ultrasonic scaler. In the conventional use of an ultrasonic scaler, the activated tip works with the bubbling action of the water spray to rapidly and gently dislodge the hard deposits and stain, while the flushing water also results in the stimulation and vigorous cleaning of the gingiva. When the ultrasonic scaler is used with the apparatus of the present invention, the compressed gas in the tank is preferably oxygen, which is bubbled through the liquid, either from the water tap or the container for the treatment solution, to dislodge the hard deposits and stain. Using oxygen as the compressed gas tends to kill anaerobic bacteria at the treatment site, and has been found to reduce inflammation and pain and to promote healing.

The novel dental apparatus can thus be more effectively used in all kinds of dental treatments, including cleaning caries, filling in preparations for crowns, filing, root canal treatment, and gum treatment for surgery and implants. The use of the treatment solution may also obviate the need to inject a local anasthetic agent.

While it is preferred to use a tank of compressed sterile oxygen, the tank may include another compressed gas, such as nitrogen, or nitrous oxide. The advantages of using sterile compressed oxygen as the gas (namely killing anaerobic bacteria at the treatment site, reducing inflammation and pain, and promoting healing) are particularly important when using the ultrasonic scaler for dislodging hard particles and for cleansing and stimulating the gingiva, but would also be present in performing other dental or other medical operations on a person.

According to a further aspect of the present invention, therefore, there is provided a method for performing an ultrasonic scaler operation on a person, characterized in vibrating the tip of an ultrasonic scaler at a high frequency of 20,000–30,000 cps while applying to the tip a mixture of a liquid and oxygen.

According to a still further aspect of the invention, there is provided a method of performing a dental or other medical operation on a person, characterized in bathing the site of the operation with gaseous oxygen from a source of compressed oxygen.

Further features and advantages of the invention will be apparent from the description below.

DESCRIPTION OF A PREFERRED EMBODIMENT

The invention is herein described, by way of example only, with reference to the accompanying single figure of drawing illustrating one form of apparatus constructed in accordance with the present invention.

The apparatus illustrated in the accompanying drawing comprises a dental unit, generally designated 2, of conventional construction such as commonly found in dental offices. It includes an air inlet pipe 4 normally coupled to a source of compressed air 6, and a water inlet pipe 8 normally connected to a source of pressurized water 10, such as the conventional water tap. The conventional dental unit 2 further includes a plurality of outlet couplings, schematically indicated at 12, 14 and 16, respectively, for coupling to various dental appliances, such as the previously-mentioned high-speed turbine drill, slow-speed drill, triple syringe and ultrasonic scaler for driving and/or cooling such appliances, or for rinsing the treatment site. The dental unit further includes an electrical heater (not shown) for heating the air and water supplied to the appliance in order to reduce patient's discomfort.

Since dental unit 2 may be one of the commercially-available units, further details of its construction and operation are not set forth. In some conventional dental units, the ultrasonic scaler is incorporated within the dental unit itself, rather than being coupled to it.

The attached drawing also illustrates a dental apparatus, generally within block 20, constructed in accordance with the present invention for use with a conventional dental unit 2. The apparatus within block 20 includes a tank 22 of a compressed sterile gas, preferably oxygen, a first selector valve $SV_1$ for selectively coupling the air inlet 4 of the dental unit either to the source of compressed air 6 or to the container 22 of compressed oxygen, a source of pressurized treatment solution 24, and a second selector valve $SV_2$ for selectively coupling the water inlet 8 of the dental unit 2 either to the water tap 10 or to the treatment solution 24.

The apparatus within block 20 includes a further selector valve $SV_3$ which permits the water inlet 8 of the dental unit 2 also to be connected to both the tank 22 of compressed gas and the container 24 for the treatment solution. This selector valve is particularly useful with an ultrasonic scaler, in order to apply a mixture of the treatment solution and oxygen via the water inlet 8 of the dental unit to the ultrasonically-vibrating tip which dislodges the calculus and stain from the teeth.

The treatment solution 24 is pressurized by a pump 26 which is automatically energized by a connection to the selector valve $SV_2$, as shown schematically by broken-line 28, when the selector valve $SV_2$ couples the treatment solution to the water inlet 8 of the dental unit 2. Pump 26 is also automaticaly energized, as indicated by the broken-line connection 29, when selector valve $SV_3$ is operated to supply a mixture of the treatment solution in container 24 and oxygen in tank 22 to the water inlet 8 of the dental unit 2. This operation is particularly advantageous when the ultrasonic scaler is being used, so that this mixture is applied to the ultrasonically-vibrating tip of the electronic scaler as it dislodges the calculus and stain, and stimulates and cleans the gingiva.

More particularly, selector valve $SV_1$ includes an inlet pipe 30 connected to the compressed air source 6 and an inlet pipe 32 connected to the oxygen tank 22, and an outlet pipe 34 connected to the air inlet 4 of the dental unit. Both inlet pipes 30 and 32 include one-way valves 36, 38, respectively, permitting the flow of the air or oxygen only into the selector valve. Both inlet pipes 30, 32 also include pressure gauges 40, 42 for measuring and indicating the pressure of the compressed air supply 6 and oxygen tank 22, respectively.

Similarly, selector valve $SV_2$ includes an inlet pipe 50 connected to the water tap 10 and another inlet pipe 52 connected to the pump 26 for the treatment solution 24, and an outlet pipe 54 connected to the water inlet 8 of the dental unit 2. Both pipes 50 and 52 include one-way valves 56, 58 permitting flow of the water or treatment solution only into the selector valve. The two pipes 50 and 52 also include pressure gauges 60, 62 for measuring and indicating the pressure in the respective pipe.

Selector valve $SV_3$ includes an inlet pipe 64 connected to inlet pipe 32 of selector valve $SV_1$ downstream of its one-way valve 38; and a second inlet pipe 66 connected to inlet pipe 52 of selector valve $SV_2$ downstream of its one-way valve 58. Selector valve $SV_3$ further includes an outlet pipe 68 connected to the outlet pipe 54 of selector valve SV$_2$ leading to the water inlet 8 of the dental unit 2.

In most applications, selector valve SV$_3$ will be closed so that the flow of the fluids will be controlled only by selector valves SV$_1$ and SV$_2$. In such applications, the operator may connect the air inlet 4 of the dental unit 2 either to the source of compressed air 6 or oxygen tank 22 by selector valve SV$_1$, and may connect the water inlet 8 of the dental unit either to the water tap 10 or the treatment solution 24 by selector valve SV$_2$.

In some applications, particularly when the ultrasonic scaler is connected to the dental unit 2, a mixture of oxygen from tank 22 and treatment solution from container 24 may be fed to the water inlet 8 of the dental unit 2, so as to produce a bubbling action of the oxygen and treatment solution to the activated tip of the ultrasonic scaler. In such applications, the two selector valves SV$_1$ and SV$_2$ would both be closed, and selector valve SV$_3$ would be opened, thereby connecting the mixture of the treatment solution from container 24 and oxygen from tank 22 via selector value SV$_3$ to the water inlet 8 of the dental unit 2.

The dental unit 2 may thus be used in the conventional manner, for driving, cooling or rinsing purposes, according to the dental appliance coupled thereto via one of the other couplings 12, 14, 16. In such case selector valve SV$_3$ would be closed; selector valve SV$_1$ would be manipulated to connect the compressed air supply 6 to the air inlet 4 of the dental unit; and selector valve SV$_2$ would be manipulated to supply the tap water 10 to the water inlet 8 of the dental unit.

When it is desired to feed the sterile oxygen in tank 22, rather than compressed air, to the air inlet 4 of the dental unit, selector valve SV$_3$ would again be closed, and selector valve SV$_1$ would be manipulated to connect its inlet pipe 32 to its outlet pipe 34; and whenever it is desired to feed treatment solution from container 24, rather than tap water to the water inlet 8 of the dental unit, selector valve SV$_3$ would remain closed, and selector valve SV$_2$ would be manipulated to connect its inlet pipe 52 to its outlet pipe 54.

In certain applications, particularly when the ultrasonic scaler is to be used, the water inlet 8 of the dental unit 2 may be supplied with a mixture of water and gas to produce a water-oxygen spray which enables the activated tip to dislodge the hard particles and to produce stimulation and cleansing of the gingiva by the flushing water. This is done in the described apparatus by closing both selector valves SV$_1$ and SV$_2$ and opening selector valve SV$_3$. In such case, the water inlet 8 of the dental unit 2 receives treatment solution from container 24 and oxygen from tank 22. The invention is particularly useful in such applications since, as indicated earlier, the use of a selected treatment solution bubbled with oxygen kills anaerobic bacteria at the treatment site and has been found to reduce inflammation and pain and to promote healing.

It will thus be seen that the apparatus illustrated in the drawing enables the dentist to provide optimum treatment to the patient for any particular case. According to the particular treatment to be performed, the dentist can not only select the appropriate dental appliance to be applied to the outlet couplings 12, 14, 16 of the dental unit, but can also select whether the dental appliance is to be supplied with compressed air from source 6 or sterile oxygen (or other gas other than air) from tank 22, or with water from tap 10, or treatment solution from container 24, by appropriately manipulating the two selector valves SV$_1$, SV$_2$. Further, by closing both selector valves SV$_1$ and SV$_2$, and opening selector valve SV$_3$, the dentist can apply a mixture of oxygen from tank 22 and treatment solution from container 24 to the water inlet 8 of the dental unit 2, which is particularly advantageous when an ultrasonic scaler is coupled to the dental unit, as described above. In addition, the dentist can provide the appropriate treatment solution within container 24 according to the particular treatment to be made to the patient.

While the system illustrated in the drawing includes the dental apparatus (within block 20) used with a conventional dental unit 2 including standard connections to the compressed air source 6 and water tap 10, it will be appreciated that the illustrated apparatus could be used without such conventional connections, whereupon only the gas from tank 22 and the treatment solution 24 would be supplied to the dental device coupled to the dental unit 2. Also, while the gas tank 22 is described as containing compressed, sterile oxygen, it will be appreciated that other gases, preferably sterile, could be used, for example nitrogen or nitrous oxide, depending upon the particular application or treatment.

Many other variations, modifications and applications of the invention will be apparent.

What is claimed is:

1. Dental apparatus for use with a dental unit having a water inlet to be coupled to a source of pressurized water for driving and/or cooling dental appliances to be coupled to the dental unit, or for flushing the treatment site, and a air inlet connectible to a source of compressed air; said dental apparatus comprising;

a tank of compressed oxygen;

a source of pressurized liquid; and valve means for coupling said tank of compressed oxygen and said source of pressurized liquid to the water inlet of the dental unit, said valve means including:

means for selectively coupling said air inlet of the dental unit to said source of compressed air or to said tank of compressed oxygen;

and means for selectively coupling said water inlet of the dental unit to said source of pressurized water, to said container for a treatment solution, or to both said container for a treatment solution and said tank of compressed oxygen.

2. The apparatus according to claim 1, wherein said source of pressurized liquid includes a container for a treatment solution, and a pump for pressurizing the treatment solution when applied to said valve means.

3. Dental apparatus for use with a dental unit having an air inlet to be coupled to a source of compressed air and a water inlet to be coupled to a source of pressurized water for driving and/or cooling dental appliances to be coupled to the dental unit; said dental apparatus comprising:

a tank of compressed oxygen;

a first selector valve for selectively coupling said air inlet of the dental unit either to said source of compressed air or to said tank of compressed gas;

a container for treatment solution;

and a second selector valve for selectively coupling said water inlet of the dental unit either to said source of pressurized water or to said container for a pressurized treatment solution.

4. The dental apparatus according to claim 3, further including a pump for pumping the treatment solution to the water inlet of the dental unit when coupled thereto by said second selector valve.

5. The dental apparatus according to claim 4, including means for automatically energizing said pump when said second selector valve couples the container for the treatment solution to the water inlet of the dental unit.

6. The dental apparatus according to claim 3, wherein said first selector valve includes an inlet pipe connected to said source of compressed air, an inlet pipe connected to said tank of compressed gas, and an outlet pipe connected to said air inlet of the dental unit;

and wherein said second selector valve includes an inlet pipe connected to said source of pressurized water, an inlet pipe connected to said container of treatment solution, and an outlet pipe connected to the water inlet of the dental unit.

7. The dental apparatus according to claim 6, wherein each of said inlet pipes includes a one-way valve permitting flow only into the respective selector valve.

8. The dental apparatus according to claim 3, wherein each of said inlet pipes includes a pressure gauge for indicating the pressure of the fluid flowing through the pipe.

9. The dental apparatus according to claim 3, further including a third selector valve permitting said water inlet of the dental unit also to be connected to both said tank of compressed gas and container for a pressurized treatment solution so as to apply a mixture of said treatment solution and pressurized gas via the water inlet to the dental appliance coupled thereto.

10. The dental apparatus according to claim 3, wherein said dental unit includes an outlet coupling for coupling an ultrasonic scaler thereto.

11. The dental apparatus according to claim 3, wherein said dental unit includes an outlet coupling for coupling a turbine-driven drill thereto.

12. The dental apparatus according to claim 3, wherein said dental unit includes an outlet coupling for coupling a triple syringe thereto.

* * * * *